United States Patent [19]

Treiber et al.

[11] 4,269,833

[45] May 26, 1981

[54] HEXAHYDRO-1,4-OXAZEPINES, THEIR PREPARATION, AND DRUGS CONTAINING THESE COMPOUNDS

[75] Inventors: Hans J. Treiber, Bruehl; Dieter Lenke, Ludwigshafen; Wolfgang Worstmann, Gruenstadt, all of Fed. Rep. of Germany

[73] Assignee: BASF Aktiengesellschaft, Fed. Rep. of Germany

[21] Appl. No.: 108,370

[22] Filed: Dec. 31, 1979

[30] Foreign Application Priority Data

Jan. 13, 1979 [DE]  Fed. Rep. of Germany ....... 2901180

[51] Int. Cl.³ ............................................ C07D 313/04
[52] U.S. Cl. ..................................... 424/244; 260/333
[58] Field of Search .......................... 424/244; 260/333

[56] References Cited

U.S. PATENT DOCUMENTS

| | | |
|---|---|---|
| 3,391,149 | 7/1968 | Easton et al. .......................... 260/333 |
| 3,729,465 | 4/1973 | Cavalla et al. .................... 260/239 B |
| 3,830,803 | 8/1974 | Klohs et al. .................... 260/239.3 B |
| 3,988,448 | 10/1976 | Bowman .............................. 260/333 |

FOREIGN PATENT DOCUMENTS 1941534  9/1970  Fed. Rep. of Germany .
1620198  9/1974  Fed. Rep. of Germany .

OTHER PUBLICATIONS

H. Griengl et al., Liebigs Ann. Chem., (1976), pp. 1791–1798.

Primary Examiner—Norma S. Milestone
Attorney, Agent, or Firm—Keil & Witherspoon

[57] ABSTRACT

Novel hexahydro-1,4-oxazepines of the general formula I

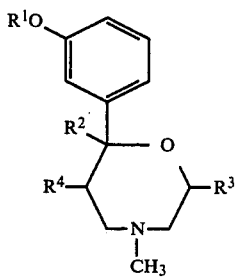

where
$R^1$ is hydrogen, or alkyl or acyl each of 1 to 4 carbon atoms,
$R^2$ is alkyl of 1 to 4 carbon atoms and
$R^3$ and $R^4$ are identical or different and each is hydrogen or methyl, and their salts with physiologically acceptable acids, processes for their preparation, drugs which contain these compounds, and their use in therapy.

The compounds may be used for the pharmacotherapy of pain of various geneses.

4 Claims, No Drawings

HEXAHYDRO-1,4-OXAZEPINES, THEIR PREPARATION, AND DRUGS CONTAINING THESE COMPOUNDS

It is known that certain nitrogen-containing heterocyclics with 7-membered and 8-membered rings possess an analgesic action. For example, amongst the group of the azepines, meptazinol (3-(3-ethyl-hexahydro-1-methyl-1H-azepin-3-yl)-phenol, disclosed in German laid-open application DOS Nos. 1,941,534), and amongst the group of the benzoxazepines, nefopam (5-methyl-1-phenyl-3,4,5,6-tetrahydro-1H-benz[f]-2,5-oxacine, disclosed in German Pat. No. 1,620,198) are known analgesics.

We have found novel oxazepine derivatives which exhibit a stronger analgesic action.

The present invention relates to hexahydro-1,4-oxazepines of the general formula I

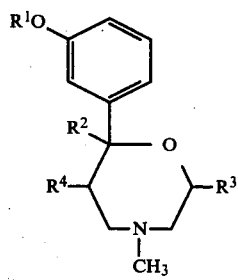

where
$R^1$ is hydrogen, or alkyl or acyl each of 1 to 4 carbon atoms,
$R^2$ is alkyl of 1 to 4 carbon atoms and
$R^3$ and $R^4$ are identical or different and each is hydrogen or methyl,
and their salts with physiologically acceptable acids.

The invention further relates to a process for the preparation of a hexahydro-1,4-oxazepine of the general formula I, wherein a compound of the general formula II

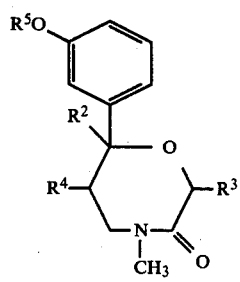

where
$R^5$ is alkyl of 1 to 4 carbon atoms and
$R^2$, $R^3$ and $R^4$ have the above meanings, is reduced and thereafter, if desired, the alkyl group $R^5$ is replaced by hydrogen or acyl, and the compound obtained is converted, if desired, to a salt with a physiologically acceptable acid.

Finally, the invention also relates to drugs which contain hexahydro-1,4-oxazepines of the general formula I.

The compounds I contain from 1 to 3 asymmetric carbon atoms, so that they can be prepared in the form of racemates or of stereoisomers. The latter may be obtained in the pure form either by asymmetric synthesis or by separation of the racemates.

The reduction of a compound II requires a powerful reducing agent, such as diborane or, preferably, lithium aluminum hydride, particularly suitable solvents being tetrahydrofuran, dioxane or diethyl ether. The reduction is carried out at an elevated temperature, preferably at the boiling point of the solvent.

The replacement of an alkoxy group on the phenyl ring by a hydroxyl group can be effected, for example, with a basic ether-cleaving compound, such as sodium methylmercaptide, in a dipolar aprotic solvent, for example hexamethylphosphorotriamide, dimethylsulfoxide or dimethylformamide, at from 50° to 200° C., preferably at from 100° to 150° C.

Virtually all conventional processes may be employed for acylating the free hydroxyl group. The simplest is the reaction with an acid anhydride or an acid halide at an elevated temperature.

The starting materials of the general formula II required for the preparation of the novel compounds have not previously been described. They may be prepared as follows:

Reaction of a ketone III with N-benzyl-N-methyl-methyleneimonium chloride IV gives a Mannich compound V (cf. Angew. Chem. 88 (1976), 261):

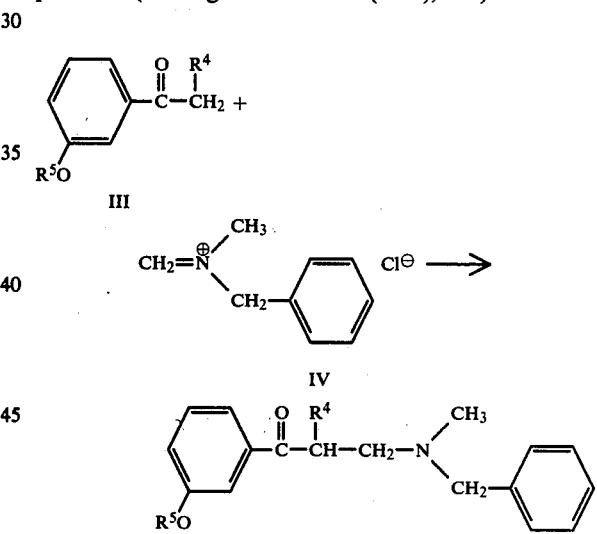

The compound V reacts with an alkyl-Grignard compound to give a compound VI (cf. J. Amer. Chem. Soc. 71 (1949), 2050)

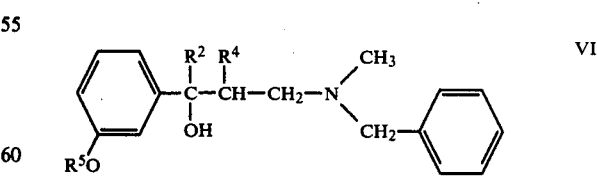

from which the benzyl radical is removed by hydrogenation.

Reaction of the debenzylated compound with chloroacetyl chloride or α-chloropropionyl chloride in the presence of dilute sodium hydroxide solution or triethylamine gives the compound

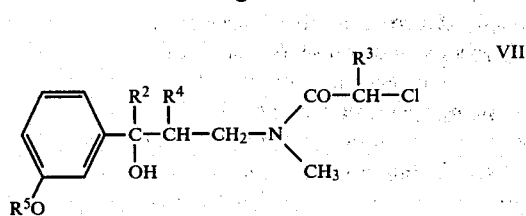

from which the compounds II may be prepared by heating with a base, such as potassium tert.-butanolate, in dimethylsulfoxide (cf. German laid-open application DOS No. 1,944,468).

The compounds according to the invention are distinguished by a pronounced analgesic action. They are therefore suitable for the pharmacotherapy of pain of different geneses.

The tail flick test of D'AMOUR and SMITH (J. Pharmacol. 72 (1941), 74–79) was used as a model for testing the analgesic action. In this experiment, the compounds to be tested (in the form of aqueous solutions, the volume injected being 10 ml/kg) were administered intraperitoneally or orally to groups of 10 female mice (NMRI strain) each weighing 19–23 g.

Pain reactions were caused by thermal irritation (focused radiation of heat from a halogen lamp onto the tail for a maximum of 30 seconds) before, and 30 minutes after, the administration of the compound.

The time which elapses before the tail is retracted, by reflex action from the irradiation zone is measured as the reaction time. In the case of 670 untreated animals it averages $6.5 \pm 0.29$ sec. Analgesic compounds lengthen the reaction time, the effects depending on the dose. There is a linear relationship between the logarithms of the doses (mg/kg) and the relative increase in the reaction time ($\Delta\%$), from which the ED 100%, i.e. the dose which doubles the reaction time, can be calculated by regression analysis. With an irradiation period of at most 30 seconds, the maximum possible increase in the reaction time is about 360%.

The analgesic action of the compounds according to the invention in the tail flick test manifests itself particularly on oral administration, ie. the form of administration which is clinically important (Table 1). The activity of the compounds is from 2 to 28 times greater than that of nefopam. The quotient of the effective dose (ED 100%) for intraperitoneal and for oral administration (0.41–0.83), which is a measure of the enteral activity, is very high. It indicates that the doses of the compounds according to the invention which are orally active are only slightly above those which are intraperitoneally active. The enteral activity is from 2.4 to 4.9 times greater than that of nefopam.

In the tail flick test, non-toxic doses of nefopam can, regardless of the route of administration, only achieve partial analgesia (192% increase in the reaction time on intraperitoneal administration, or 93% on oral administration). At higher doses, nefopam is toxic and produces a high mortality rate. In contrast, with the compounds according to the invention the reaction time can be lengthened to substantially higher maximum values (by 276–435% on intraperitoneal administration and by 223–419% on oral administration), without producing toxic effects.

TABLE 1

| Compound of Ex. No. | Intraperitoneal administration | | | | Oral administration | | | | |
|---|---|---|---|---|---|---|---|---|---|
| | ED 100%[1] | Relative activity | Maximum action[2] mg/kg | % | ED 100% | Relative activity | Maximum action mg/kg | % | Q[3] |
| 2 | 12.7 | 0.64 | 46.4 | 332 | 22.4 | 2.07 | 100 | 333 | 0.57 |
| 1 | 1.71 | 4.73 | 10.0 | 276 | 2.07 | 22.42 | 10.0 | 387 | 0.83 |
| 6 | 6.83 | 1.18 | 46.4 | 326 | 8.71 | 5.33 | 46.4 | 419 | 0.78 |
| 7 | 0.675 | 11.97 | 4.64 | 382 | 1.66 | 27.95 | 4.64 | 300 | 0.41 |
| 3 | 6.58 | 1.23 | 21.5 | 351 | 15.3 | 3.03 | 46.4 | 223 | 0.43 |
| 4 | 4.43 | 1.82 | 21.5 | 319 | 6.27 | 7.40 | 100 | 397 | 0.71 |
| 5 | 5.66 | 1.43 | 46.4 | 435 | 7.01 | 6.62 | 21.5 | 318 | 0.81 |
| 9 (+) | 2.08 | 3.89 | 10.0 | 339 | 2.76 | 16.81 | 10.0 | 310 | 0.75 |
| Nefopam | 8.08 | ≡1.00 | 21.5[4] | 192 | about 46.4 | ≡1.00 | 46.4[5] | 93 | 0.17 |

[1] Dose (mg/kg) which lengthens the reaction time by 100%
[2] Maximum possible increase in the reaction time, for a dose interval of $\sqrt[3]{10}$
[3] Q = enteral activity = ED 100% for intraperitoneal administration/ED 100% for oral administration
[4] Toxic at 46.4 mg/kg (6 out of 10 animals die)
[5] Toxic at 100 mg/kg (6 out of 10 animals die)

The compounds according to the invention can be administered in a conventional manner, orally or parenterally (subcutaneously, intravenously, intramuscularly or intraperitoneally).

The dosage depends on the age, condition and weight of the patients and on the route of administration. As a rule, the daily dose of active compound is from about 0.01 to 1.0 mg/kg on intravenous, subcutaneous, intramuscular or oral administration. This dose is administered in from 1 to 3 portions over the course of the day. In severe cases, administration may be even more frequent.

The novel compounds may be employed in the conventional solid or liquid pharmaceutical forms for administration, for example as tablets, capsules, powders, granules, dragees, solutions or suppositories. These are produced in a conventional manner. The active compounds can be mixed with the conventional pharmaceutical auxiliaries, such as tablet binders, fillers, preservatives, tablet disintegrating agents, flow regulators, plasticizers, wetting agents, dispersants, emulsifiers, solvents, retarders and/or antioxidants (cf. L. G. Goodman and A. Gilman: The Pharmacological Basis of Therapeutics).

The novel compounds may also be administered in the form of their salts with physiologically acceptable acids. Examples of such acids are hydrochloric acid, sulfuric acid, phosphoric acid, tartaric acid, citric acid, fumaric acid, acetic acid, formic acid, succinic acid, maleic acid, lactic acid and amidosulfonic acid.

Preparation of the starting materials (a)

β-(N-Benzyl-N-methyl)-amino-3-methoxypropiophenone hydrochloride.

60 g of 3-methoxyacetophenone (0.4 mole) and 70 g of N-benzyl-N-methyl-methyleneimonium chloride (0.4 mole) (prepared from bis-(benzylmethylamino)-methane and acetyl chloride) in 500 ml of dry acetonitrile are heated, whilst stirring, for 60 minutes at 75° C. and then for 15 minutes at 80° C. The solution is cooled and introduced into 2 liters of ether, the product is filtered off and 88 g (69% of theory) of a compound of melting point 134°–138° C. are obtained; this can be recrystallized from isopropanol or can be used in the crude form for the subsequent reaction.

Melting point, after recrystallization from isopropanol: 140°–142° C.

β-(N-Benzyl-N-methyl)-amino-α-methyl-3-methoxypropiophenone hydrochloride is prepared similarly from 3-methoxypropiophenone. Melting point 125° C.

(b)

1-(N-Benzyl-N-methyl)-amino-3-hydroxy-3-(3-methoxyphenyl)-pentane 170 g (0.53 mole) of β-(N-benzyl-N-methyl)-amino-3-methoxypropiophenone hydrochloride (obtained as described in (a)) are introduced, whilst stirring and cooling with an icebath, into a Grignard solution which has been prepared from 218 g (2.0 moles) of ethyl bromide, 48 g (2.0 moles) of magnesium and 1.5 liters of dry ether; the mixture is refluxed for 2–3 hours and is then stirred overnight at room temperature, after which the batch is decomposed with ammonium chloride solution. The ether phase is separated off and dried with sodium sulfate, the ether is distilled off and the residue is fractionated under reduced pressure.

Yield 134 g (81% of theory). Boiling point 180°–190° C./0.01 mbar.

The following are obtained by a similar method:
1-(N-Benzyl-N-methyl)-amino-3-hydroxy-3-(3-methoxyphenyl)-butane, boiling point 175°–180° C./0.01 mbar,
1-(N-benzyl-N-methyl)-amino-3-hydroxy-3-(3-methoxyphenyl)-hexane, boiling point 185°–195° C./0.01 mbar and
1-(N-benzyl-N-methyl)-amino-2-methyl-3-hydroxy-3-(3-methoxyphenyl)-pentane, boiling point 180°–185° C./0.01 mbar.

(c)

1-Methylamino-3-hydroxy-3-(3-methoxyphenyl)-pentane 78.6 g (0.25 mole) of 1-(N-benzyl-N-methyl)-amino-3-hydroxy-3-(3-methoxyphenyl)-pentane (prepared as described in (b)) are dissolved in 400 ml of methanol and are hydrogenated in the presence of 8 g of 10% strength palladium-on-charcoal catalyst under atmospheric pressure at room temperature. After the absorption of hydrogen has ended, the catalyst is filtered off, the solution is evaporated and the product is obtained as an oil which crystallizes.

Yield: 53 g (94% of theory). Melting point, after recrystallization from hexane: 52°–54° C.

The following are obtained by similar methods:

1-Methylamino-3-hydroxy-3-(3-methoxyphenyl)-butane (used in the crude form for further conversion),
1-methylamino-3-hydroxy-3-(3-methoxyphenyl)-hexane, melting point, after recrystallization from hexane: 70°–72° C., and
1-methylamino-2-methyl-3-hydroxy-3-(3-methoxyphenyl)-pentane (used in the crude form for further conversion).

(d)

1-(N-Chloroacetyl)-methylamino-3-hydroxy-3-(3-methoxyphenyl)-pentane 100 ml of 2 N sodium hydroxide solution are added to a solution of 35 g (0.16 mole) of 1-(methylamino-3-hydroxy-3-(3-methoxyphenyl)-pentane (obtained as described in (c)) in 250 ml of ether, and 18 g (0.16 mole) of chloroacetyl chloride are then added dropwise in the course of 30 minutes, whilst stirring. The mixture is then heated for 90 minutes, the ether layer is separated off and dried with sodium sulfate, and the solvent is distilled off. The residue is used in the crude form for further conversion.

The following are obtained by similar methods:
1-(N-Chloroacetyl)-methylamino-3-hydroxy-3-(3-methoxyphenyl)-butane,
1-(N-chloroacetyl)-methylamino-3-hydroxy-3-(3-methoxyphenyl)-hexane and
1-(N-chloroacetyl)-methylamino-2-methyl-3-hydroxy-3-(3-methoxyphenyl)-pentane.

If α-chloropropionyl chloride is used, 1-(N-α-chloropropionyl)-methylamino-3-hydroxy-3-(3-methoxyphenyl)-pentane is obtained.

(e)

7-Ethyl-7-(3-methoxyphenyl)-4-methyl-hexahydro-1,4-oxazepin-3-one 41.4 g (0.14 mole) of 1-(N-chloroacetyl)-methylamino-3-hydroxy-3-(3-methoxyphenyl)-pentane, obtained as described in (d), are dissolved in 200 ml of dimethylsulfoxide and 33.6 g of potassium tert.-butanolate are added in portions at 20° C. whilst stirring and gently cooling the mixture. The mixture is then heated at 50° C. for 30–120 minutes, after which it is stirred overnight at room temperature. The mixture is worked up either by distilling off the solvent under reduced pressure at as low a temperature as possible, or by diluting the batch with 1.5 liters of water and extracting it with 3×250 ml of methylene chloride. The solvent is removed after drying over sodium sulfate, giving a crude product which is used, as obtained, for further processing.

The following are obtained by similar methods:
4,7-Dimethyl-7-(3-methoxyphenyl)-hexahydro-1,4-oxazepin-3-one; the compound crystallizes, melting point 88°–94° C.,
7-(3-methoxyphenyl)-4-methyl-7-propyl-hexahydro-1,4-oxazepin-3-one,
4,6-dimethyl-7-ethyl-7-(3-methoxyphenyl)-hexahydro-1,4-oxazepin-3-one and
2,4-dimethyl-7-ethyl-7-(3-methoxyphenyl)-hexahydro-1,4-oxazepin-3-one.

Preparation of the end products

EXAMPLE 1

7-Ethyl-7-(3-methoxyphenyl)-4-methyl-hexahydro-1,4-oxazepine 36 g (0.14 mole) of crude 7-ethyl-7-(3-methoxyphenyl)-4-methyl-hexahydro-1,4-oxazepine (cf. e) are dissolved in 100 ml of absolute tetrahydrofuran and the solution is added dropwise to a suspension of 15 g of lithium aluminum hydride in 500 ml of absolute tetrahydrofuran, at the boil. The mixture is then boiled for 6 hours, cooled and decomposed with water in a conventional manner; after filtering off the inorganic residue, drying the filtrate and distilling off the solvent, the crude base is obtained, which is converted to its hydrochloride by means of a solution of hydrochloric acid in isopropanol.

Yield of hydrochloride 15 g (38% of theory), melting point 181°–183° C.

The compounds tabulated below are obtained by similar methods:

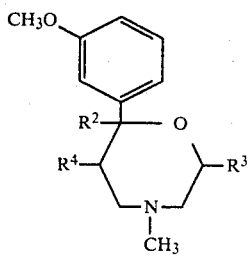

| Example No. | $R^2$ | $R^3$ | $R^4$ | Hydrochloride Melting point, °C. | Yield, % |
|---|---|---|---|---|---|
| 2 | $CH_3$ | H | H | 207–208 | 32 |
| 3 | $C_3H_7$ | H | H | 199–201 | 33 |
| 4 | $C_2H_5$ | $CH_3$ | H | 185–187 | 28 |
| 5 | $C_2H_5$ | H | $CH_3$ | 202–203 | 47 |

EXAMPLE 6

4,7-Dimethyl-7-(3-hydroxyphenyl)-hexahydro-1,4-oxazepine

A solution of sodium methylmercaptide in ethanol is prepared from 2.3 g (0.1 mole) of sodium, 100 ml of absolute ethanol and 6.2 g (0.1 mole) of ethylmercaptan, the alcohol is distilled off under reduced pressure, 50 ml of dry dimethylformamide and 5.1 g (0.02 mole) of 4,7-dimethyl-7-(3-methoxyphenyl)-hexahydro-1,4-oxazepine (base) (obtained as described in Example 1) are added and the batch is heated at 140° C. for 3 hours. It is then diluted with 500 ml of water and neutralized with acetic acid, and the solution is repeatedly extracted with methylene chloride. After removing the solvent from the extract, the residue is taken up in 100 ml of ether and the product is precipitated as the hydrochloride by introducing hydrogen chloride gas into the solution. The hydrochloride is recrystallized from ethanol.

Yield: 2.7 g (53% of theory). Melting point 248° C.
The following are obtained by similar methods:

EXAMPLE 7

7-Ethyl-7-(3-hydroxyphenyl)-4-methyl-hexahydro-1,4-oxazepine, melting point 204°–206° C.

EXAMPLE 8

7-(3-Acetoxyphenyl)-7-ethyl-4-methyl-hexahydro-1,4-oxazepine 2.7 g (0.01 mole) of the 7-ethyl-7-(3-hydroxyphenyl)-4-methyl-hexahydro-1,4-oxazepine hydrochloride obtained as described in Example 2 are boiled with 25 ml of acetic anhydride for 3 hours. The excess acetic anhydride is then distilled off under reduced pressure and the residue is recrystallized from an isopropanol/ether mixture.

Yield: 2.4 g of the hydrochloride (75% of theory). Melting point 210° C.

EXAMPLE 9

(+)- and (−)-7-Ethyl-7-(3-methoxyphenyl)-4-methyl-hexahydro-1,4-oxazepine (separation of the racemate)

A solution of 12 g (0.05 mole) of racemic 7-ethyl-7-(3-methoxyphenyl)-4-methyl-hexahydro-1,4-oxazepine (cf. Example 1) and 17 g (0.05 mole) of L-(−)-0,0-dibenzoyltartaric acid monohydrate in 50 ml of isopropanol and 10 ml of diisopropyl ether is prepared; after some time, the salt of the dextrorotatory base crystallizes out. After recrystallizing this 3 or 4 times from a 5-fold amount of isopropanol, 6 g (about 40% of theory) of a product of constant optical rotation are obtained.

Specific rotation: $[\alpha]_{589\ nm}^{20} = -45°$ (c=10 mg/ml in ethanol).

The base is obtained from the salt in a conventional manner and is converted to its hydrochloride.

If D-(+)-0,0-dibenzoyltartaric acid is used for separating the racemate, the dibenzoyltartrate of the levorotatory base is obtained similarly. Specific rotations:
bases: $[\alpha]_{589}^{20} = +/-35°$ (c=28 mg/ml in ethanol)
hydrochlorides: $[\alpha]_{589}^{20} = +/-44°$ (c=10 mg/ml in ethanol)

Melting point 202°–203° C.

EXAMPLE 10

Tablets of the following composition are produced in a conventional manner on a tableting press:
10.00 mg of 7-ethyl-7-(3-methoxyphenyl)-4-methyl-hexahydro-1,4-oxazepine hydrochloride
50.00 mg of corn starch
4.50 mg of gelatin
15.00 mg of lactose
7.50 mg of talc
0.75 mg of Aerosil ® (chemically pure silica in a submicroscopic state of division) and
2.25 mg of potato starch (as a 6% strength paste). cl EXAMPLE 11

Dragees of the following composition are prepared in a conventional manner:
10.00 mg of 7-ethyl-7-(3-methoxyphenyl)-4-methyl-hexahydro-1,4-oxazepine hydrochloride
50.00 mg of core composition
40.00 mg of sugar-coating composition.

The core composition consists of 9 parts of corn starch, 3 parts of lactose and 1 part of Luviskol ® VA 64 (a 60:40 vinylpyrrolidone/vinyl acetate copolymer, cf. Pharm. Ind. 1962, 586). The sugar-coating composition consists of 5 parts of cane sugar, 2 parts of corn starch, 2 parts of calcium carbonate and 1 part of talc. The dragees thus produced are then provided with a coating resistant to gastric juices.

EXAMPLE 12

5 g of 7-ethyl-7-(3-methoxyphenyl)-4-methyl-hexahydro-1,4-oxazepine hydrochloride are dissolved in 2.0 liters of water, sodium chloride is added to make the solution isotonic, and the latter is sterile-packed in ampoules of 2 ml capacity.

We claim:

1. A hexahydro-1,4-oxazepine of the general formula

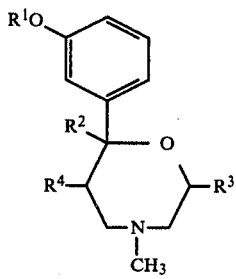

where
R$^1$ is hydrogen, or alkyl or acyl each of 1 to 4 carbon atoms,
R$^2$ is alkyl of 1 to 4 carbon atoms and
R$^3$ and R$^4$ may be identical or different and each is hydrogen or methyl,
and its salts with physiologically acceptable acids.

2. A compound selected from the group comprising 7-ethyl-7-(3-methoxyphenyl)-4-methyl-hexahydro-1,4-oxazepine, (+)-7-ethyl-7-(3-methoxyphenyl)-4-methyl-hexahydro-1,4-oxazepine, (−)-7-ethyl-7-(3-methoxyphenyl)-4-methyl-hexahydro-1,4-oxazepine, 4,7-dimethyl-7-(3-methoxyphenyl)-hexahydro-1,4-oxazepine, 7-(3-methoxyphenyl)-4-methyl-7-propyl-hexahydro-1,4-oxazepine, 2,4-dimethyl-7-ethyl-7-(3-methoxyphenyl)-hexahydro-1,4-oxazepine, 4,6-dimethyl-7-ethyl-7-(3-methoxyphenyl)-hexahydro-1,4-oxazepine, 4,7-dimethyl-7-(3-hydroxyphenyl)-hexahydro-1,4-oxazepine, 7-ethyl-7-(3-hydroxyphenyl)-4-methyl-hexahydro-1,4-oxazepine and 7-(3-acetoxyphenyl)-7-ethyl-4-methyl-hexahydro-1,4-oxazepine.

3. A therapeutic composition for alleviating pain comprising a pharmaceutical excipient and an effective amount of a compound according to claim 1 as the active ingredient.

4. The method of alleviating pain in a patient suffering therefrom which comprises administering an effective amount of a compound according to claim 1.